United States Patent [19]
Fenelli

[11] Patent Number: 5,633,391
[45] Date of Patent: May 27, 1997

[54] METHYLTRIOXORHENIUM-BIS(TRIMETHYLSILYL)PEROXIDE EPOXIDATION OF OLEFINS

[75] Inventor: Steven P. Fenelli, Hillsborough, N.J.

[73] Assignee: National Starch and Chemical Investment Holding Corporation, Wilmington, Del.

[21] Appl. No.: 631,389

[22] Filed: Apr. 12, 1996

[51] Int. Cl.$^6$ .................................. C07D 301/14
[52] U.S. Cl. .................................................. 549/525
[58] Field of Search ........................... 549/525; 502/152

[56] References Cited

U.S. PATENT DOCUMENTS 5,155,247  10/1992  Herrmann et al. ..................... 556/46
5,166,372  11/1992  Crocco et al. ......................... 549/531

OTHER PUBLICATIONS

Irie, R. et al., "Enantioselective Epoxidation of Chromene Derivatives Using Hydrogen Peroxide as a Terminal Oxidant", Synlett, 4, pp. 255–256, 1994.

Herrmann, W. A., et al., "Methyltrioxorhenuim as a Catalyst for Olefin Oxidation", Angew. Chem. Int. Ed. Engl., 30(12), pp. 1638–1641, 1991.

Adam, Waldemar and Mitchell Caterine M., "Methyltrioxorhenium (VII)–Catalyzed Epoxidation of Alkenes with the Urea/Hydrogen Peroxide Adduct", Amgew. Chem. Int. Ed. Engl. 1996, 35, No. 5, pp. 533–534.

"Epoxidation of Allyl and Homoallyl Trimethylsilyl Ethers with t–Butyldioxytrimethylsilane and Silicon Lewis Acid/Vanadium Catalyst", Tamejiro Hiyama, et al., Tetrahedron Letters, vol. 24, No. 4, pp. 395–398, 1983.

"Enantioselective Epoxidation of Chromene Derivatives Using Hydrogen Peroxide as a Terminal Oxidant", Ryo Irie, et al., Synlett, (1994), pp. 255–256.

"Methyltrioxorhenium as a Catalyst for Olefin Oxidation", Wolfgang A. Herrmann, et al., Angew. Chem. Int. Ed. Engl. 30 (1991), No. 12, pp. 1638–1641.

"Dissociation of Hydrogen Peroxide Adducts in Solution: The Use of Such Adducts for Epoxidation of Alkenes", Antonio M. d'A. Rocha Gonsalves, et al., J. Chem. Research (S), (1991) pp. 208–209.

"A Very Simple Oxidation of Olefins and Ketones with UHP–Maleic Anhydride", Luis Astudillo, et al., Heterocycles, vol. 36, No. 5, 1993, pp. 1075–1080.

*Primary Examiner*—C. Warren Ivy
*Assistant Examiner*—Lyman H. Smith
*Attorney, Agent, or Firm*—Jane E. Gennaro

[57] ABSTRACT

A process for the epoxidation of olefins comprises contacting the olefin with bis(trimethylsilyl)peroxide in the presence of a rhenium catalyst in an organic solvent.

3 Claims, No Drawings

METHYLTRIOXORHENIUM-BIS(TRIMETHYLSILYL)PEROXIDE EPOXIDATION OF OLEFINS

FIELD OF THE INVENTION

The present invention relates to the epoxidation of olefins with rhenium (VII) complexes.

BACKGROUND OF THE INVENTION

The epoxidation of olefins utilizing hydrogen peroxide as the oxidant is a widely practiced method to make epoxy compounds. In recent years, rhenium complexes have been reported as effective catalysts with hydrogen peroxide. However, this procedure has been shown to require anhydrous hydrogen peroxide. Hydrogen peroxide is commercially available only in the form of aqueous solutions, and aqueous conditions tend to favor further reaction of the epoxide to give the diol. Thus, the procedures in the open literature in which rhenium (VII) is used take steps to dry the hydrogen peroxide solution in an alcohol prior to its use.

For example, U.S. Pat. No. 5,155,247 issued on Oct. 13, 1992, teaches the epoxidation of olefins using rhenium (VII) complexes in conjunction with hydrogen peroxide under near anhydrous conditions. The water in the hydrogen peroxide solution is removed by diluting the aqueous solution with tert-butyl alcohol, drying the solution over anhydrous magnesium sulfate, and removing the hydrated salt by filtration. The rhenium complex is then added to the alcoholic hydrogen peroxide solution followed by the addition of the olefin to carry out the epoxidation. The reaction must be conducted at relatively low temperatures, for example, −30° C. to +10° C., so that the oxidation leads selectively to the epoxide and further reaction to form the diol is suppressed. The required steps to provide the anhydrous conditions and the requirement of low temperatures under which the reaction is carried out make this procedure impractical on a commercial scale.

U.S. Pat. No. 5,166,372 issued on Nov. 24, 1992, describes the use of nitrogen containing heterocycles as ligands to rhenium catalysts used with hydrogen peroxide to epoxidize olefins. The reference claims that this class of organorhenium oxide catalysts tends to produce the lowest levels of undesired 1,2-diol side-products formed by hydrolysis. However, these compounds also modulate the activity of the catalysts downward, and thus slow the reaction rate considerably. The disclosed epoxidation method further employs a secondary alkyl aryl alcohol in combination with molecular oxygen to produce the hydrogen peroxide in situ. One of the byproducts of this reaction is the corresponding alkyl aryl ketone, which must then be hydrogenated over a platinum or palladium catalyst to convert it back to the alkyl aryl alcohol. In addition, the water content of the reaction mixture is sought to be maintained below four weight percent, and most preferably below one weight percent, by removing water formed during the oxidation from the reaction vessel with unreacted oxygen and inert gases. As can be understood, this technology requires specialized equipment that makes the method commercially unattractive.

SUMMARY OF THE INVENTION

This invention is a process for epoxidizing olefins that does not require the drying of hydrogen peroxide, or the use of catalysts with nitrogen containing ligands, or specialized equipment and conditions to reduce or eliminate the formation of undesired glycols.

The process comprises reacting the olefin with bis(trimethylsilyl) peroxide, $(CH_3)_3SiO{-}O{-}O{-}Si(CH_3)_3$, in an organic solvent in the presence of an organorhenium VII oxide catalyst under ambient conditions of temperature and pressure.

The utilization of bis(trimethylsilyl) peroxide as the source of hydrogen peroxide for epoxidation of olefin formation provides anhydrous peroxide without the need for specialized apparatus or drying procedures. In addition, it effectively suppresses diol formation, and obviates the need to titrate to determine the peroxide concentration.

Although hydrogen peroxide can function as an oxygen transfer agent for the oxidation of olefins, organic peroxides typically undergo homolytic cleavage of the oxygen-oxygen bond and do not function as oxygen transfer agents even in combination with transition metal catalysts. Thus, it was unexpected that bis(trimethylsilyl) peroxide can be used in combination with organorhenium VII complexes to epoxidize olefins. In addition, it has also been found that both improved conversions and faster reaction rates are obtained when urea is added at a level equal to the molar amount of rhenium VII complex.

DETAILED DESCRIPTION OF THE INVENTION

The preparation of the requisite rhenium complex can be accomplished by the synthetic route illustrated by equation (1):

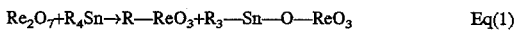

$$Re_2O_7 + R_4Sn \rightarrow R{-}ReO_3 + R_3{-}Sn{-}O{-}ReO_3 \qquad Eq(1)$$

An additional improvement in the chemistry outlined in equation (1) is obtained on adding a perfluorinated anhydride prior to the tetraalkyltin compound, which allows for conversion of the trialkylstanyl perrhenate into the desired alkyltrioxorhenium complex, as outlined in equation (2):

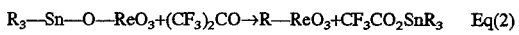

$$R_3{-}Sn{-}O{-}ReO_3 + (CF_3)_2CO \rightarrow R{-}ReO_3 + CF_3CO_2SnR_3 \qquad Eq(2)$$

Any organorhenium oxide compound that is active as an epoxide catalyst for the hydrogen peroxide oxidation of an olefin may be employed in the process of this invention. The most commonly used rhenium complex is that in which $R=CH_3$, methyltrioxorhenium (hereinafter MTO), which is stable under ambient conditions. A detailed synthetic method for methyltrioxorhenium is given in U.S. Pat No. 5,155,247 at column 8.

Briefly, the procedure and exemplary reagent amounts are as follows: All solvents must be thoroughly dried before use. The reaction vessel is dried at 400°–600° C. under high vacuum before weighing in the starting material, 10.00 g, (20.64 mmol) of dirhenium heptoxide, $Re_2O_7$. Tetrahydrofuran, 90 ml, is added with vigorous stirring to dissolve the $Re_2O_7$, followed by the addition of commercially available tetramethylstannane, $Sn(CH_3)_4$, 3.15 ml (22.71 mmol). This reagent is toxic and all operations must be carried out with suitable precautions. The reaction mixture is then heated at reflux for four hours. The solution is cooled to room temperature and the solvent slowly removed under reduced pressure until the residue has a paste-like consistency. At this point the reaction apparatus is provided with a cold finger condenser cooled to between −10° C. and 0° C. to prevent excessive sublimation of the target rhenium complex. After the solvent is completely removed, the product is isolated in the form of colorless needles at about 80° C. by sublimation under vacuum.

Alternatively, the methyltrioxorhenium complex can be obtained commercially from Aldrich Chemical, catalogue #41,291-0.

Bis(trimethylsilyl) peroxide is a colorless liquid compound having the structural formula:

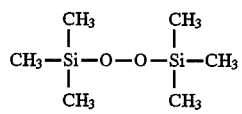

It can be obtained from Gelest, Inc., of Tullytown, Pa.

The epoxidation preferably is carried out by the addition of the olefin to a solution of bis(trimethylsilyl) peroxide in tert-butyl alcohol that also contains the dissolved rhenium complex. The reaction can be conducted at ambient temperature and pressure.

The amount of catalyst is not critical, but should be sufficient to accomplish the desired epoxidation reaction in a short period of time. The optimum quantity will depend upon a number of factors, including reaction temperature, olefin reactivity and concentration, and hydrogen peroxide concentration. The amount of bis(trimethylsilyl) peroxide relative to the amount of olefin is not critical, provided that at least one equivalent of hydrogen peroxide is present per equivalent of a mono-unsaturated olefin. It is, however, preferable to use an excess of the peroxide to optimize the yield of epoxide; nevertheless, as will be understood by those skilled in the art, it is preferable to use as low an amount of excess hydrogen peroxide as possible and still accomplish an efficient conversion.

Typically, the molar ratio of bis(trimethylsilyl) peroxide to olefin to MTO will be in the range from 1200:120:1 to 300:120:1, with the rhenium catalyst present at a level of 0.5–5.0 mole percent with respect to olefin. Preferably the ratio will be about 600:120:1, and more preferably will be about 300:120:1.

This process may be used to epoxidize any organic compound having at least one ethylenically unsaturated functional group (carbon-carbon double bond), and may be aromatic, aliphatic, mixed aromatic-aliphatic, cyclic, branched or straight chain. The process is especially useful for the epoxidation of olefins having 2 to 30 carbon atoms.

Suitable solvents for the reaction medium include tetrahydrofuran, monovalent aliphatic alcohols with 1–5 carbon atoms, and aromatic hydrocarbons, such as, toluene and xylene. The preferred solvent for the reaction is tertiary-butyl alcohol.

The following examples are given to illustrate the invention further, and should not be deemed as a limitation on the scope of the invention.

EXAMPLES

Example I

A series of epoxides was prepared using bis(trimethylsilyl peroxide as the oxidant in the presence of methyltrioxorhenium (MTO) catalyst according to the procedure:

To a 50 ml multinecked flask fitted with a reflux condenser, thermometer, and magnetic stirrer were charged 4.40 g (0.03 mol) of bis(trimethylsilyl) peroxide, 15 ml of tert-butyl alcohol, and 25 mg of methyltrioxorhenium (MTO). The resulting slurry was allowed to stir for 5 minutes and then the olefin was added in a molar ratio of peroxide:olefin:MTO of 300:120:1. The mixture was stirred at room temperature (25° C.) until reaction was judged by gas chromatography to be complete, which is the time reported.

The results are tabulated in Table I. Yields are given as normalized area percents of components (olefin, epoxide, and diol) obtained by gas chromatography, and may be considered as weight ratios.

TABLE I

| Olefin substrate | Time (hours) | Epoxide % yield | Diol % yield |
|---|---|---|---|
| cyclododecene | 1 | cyclododecane oxide > 98% | <1% |
| cyclohexene | 2.5 | cyclohexane oxide > 98% | <1% |
| allyl benzene | 40 | 2,3-epoxypropylbenzene 77% | 1.9% |
| phenyl allyl ether | 72 | phenyl glycidyl ether 36% | <1% |

A similar series of epoxidations was run using the molar ratio of peroxide: olefin: catalyst of 230:120:1. This represents a 25% reduction in peroxide and resulted in only an increase of only about 0.5–1 hour in the time required to obtain quantitative conversion of the cyclododecene and cyclohexene.

Example II

Comparative Epoxidations.

The epoxidation of allyl benzene using aqueous hydrogen peroxide gave lower selectivity to the epoxide, higher diol formation, and longer reaction times compared to the process as embodied in Example I. Water was initially removed by drying a mixture of t-butanol, α-methylbenzyl alcohol (α-MeBzOH), and 30% hydrogen peroxide ($H_2O_2$) over anhydrous magnesium sulfate, followed by removal of the hydrated salt by filtration. After titrimetric determination of both water content and active oxygen, the appropriate volume of solution was added to a multinecked flask, followed by the addition of MTO and allylbenzene. The reagents were admixed as described above in a mole ratio of $H_2O_2$:AB:MTO::112:30:1 (a higher ratio of peroxide to olefin than in Example I), and after 43 hours at 25° C. the reaction yielded 46% of the epoxide and 7.4% of the diol by-product. A second reaction was conducted for four (4) hours at 45° C. and yielded 61% of the epoxide and 17% of the diol.

Example III

Comparative Epoxidations.

The epoxidation of allyl phenyl ether using aqueous hydrogen peroxide and methyltrioxorhenium (MTO) catalyst in the presence of a secondary alkyl aryl alcohol also gave lower selectivity to the epoxide than with bis(trimethylsilyl) peroxide. A mixture of t-butanol, α-methylbenzyl alcohol (α-MeBzOH), and 30% hydrogen peroxide ($H_2O_2$) were dried over anhydrous magnesium sulfate, followed by removal of the hydrated salt by filtration. After titrimetric determination of both water content and active oxygen, the appropriate volume of solution was added to a multinecked flask, followed by the addition of MTO and allyl phenyl ether. The reaction stirred for eight hours. Although none of the diol, 3-phenoxy-1,2-propanediol, was detected in any of the reaction mix that the yields of epoxides were less than 10%. In addition, the experiments carried out in the presence of the α-methylbenzyl alcohol (α-OH) gave no improvement in yield over those in which it was absent. The mole ratios of $H_2O_2$:APE:MTO, the presence of α-MeBzOH, the reaction temperature, and percent yield (as a weight ratio of olefin, epoxide, and diol, using gas chromatography) are reported in Table II.

TABLE II

| Mole Ratio | | | Reaction Conditions | | | Mol % Yield |
|---|---|---|---|---|---|---|
| $H_2O_2$ | APE | MTO | α-OH | °C. | Hours | % Oxide |
| 300 | 125 | 1 | yes | 25 | 8 | <1 |
| 300 | 125 | 1 | yes | 50 | 8 | 5.6 |
| 300 | 125 | 1 | yes | 60 | 8 | 5.1 |
| 300 | 120 | 1 | no | 25 | 8 | 7.6 |
| 200 | 85 | 1 | yes | 25 | 8 | 8.3 |
| 200 | 85 | 1 | no | 25 | 8 | 9.9 |

Example IV

A series of epoxidations was run on allyl benzene varying the ratio of rhenium catalyst to olefin and increasing the reaction temperature, otherwise the epoxidations were carried out according to the procedure in Example I. The results are given in Table III, and yields are normalized as obtained from gas chromotography.

TABLE III

| Ratio peroxide:AB:MTO | Temperature °C. | Percent Epoxide |
|---|---|---|
| 300:125:1 | 30° | 44% |
| 300:125:1 | 40° | 66% |
| 300:125:1 | 50° | 56% |
| 300:125:1.25 | 30° | 47% |
| 300:125:1.25 | 40° | 52% |

The data indicate that an improvement in conversion is obtained on increasing the ratio of the rhenium catalyst to olefin. A more significant increase is obtained on increasing temperature to 40° C., although at temperatures higher than 40° C. a loss in conversion is observed.

Example V

Comparative Epoxidations.

Reactions were conducted to epoxidize cyclododecene (chosen because it is usually very easily epoxidized) according to the procedure of Example I, with the exception that in one reaction di-t-butyl peroxide was used in place of bis(t-rimethylsilyl) peroxide, and in a second reaction O-trimethylsily-t-butyl peroxide was used. No change in the olefin was detected. This example shows that the bis(trimethylsilyl) peroxide is needed to accomplish the epoxidation.

These examples show that bis(trimethylsilyl) peroxide in the presence of a rhenium VII catalyst is an effective epoxidizing reagent for olefins.

I claim:

1. A process for the epoxidation of olefins comprising contacting the olefin with bis(trimethylsilyl)peroxide in the presence of a rhenium oxide catalyst in an organic solvent.

2. The process according to claim 1 in which the mole ratio of bis(trimethylsilyl)peroxide:olefin: rhenium catalyst is about 300:120:1.

3. The process according to claim 1 in which the rhenium catalyst is methyltrioxorhenium.

* * * * *